United States Patent
Acosta-Geraldino et al.

(10) Patent No.: US 6,853,305 B2
(45) Date of Patent: Feb. 8, 2005

(54) AIR-CONDUIT CONDENSATION SENSOR

(75) Inventors: Mariel Acosta-Geraldino, Tucson, AZ (US); Diana Joyce Hellman, Tucson, AZ (US); Wayne Alan McKinley, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 198 days.

(21) Appl. No.: 10/156,418

(22) Filed: May 28, 2002

(65) Prior Publication Data

US 2003/0222663 A1 Dec. 4, 2003

(51) Int. Cl.$^7$ .............................................. G08B 21/00
(52) U.S. Cl. ................... 340/604; 340/602; 340/605; 340/620; 340/693.6; 324/634; 324/640; 324/689; 324/694; 73/304 R; 73/29.01; 200/61.04; 200/61.06; 200/185
(58) Field of Search ................................ 340/602, 603, 340/604, 605, 620, 693.6; 73/336.5, 336, 335.14, 29.03; 324/65, 634, 640, 694, 693

(56) References Cited

U.S. PATENT DOCUMENTS

| | | | |
|---|---|---|---|
| 3,424,977 A | * 1/1969 | Hans ........................... 324/689 |
| 4,023,206 A | 5/1977 | Nishibe et al. ................ 360/75 |
| 4,127,763 A | * 11/1978 | Roselli ........................ 219/203 |
| 4,553,432 A | 11/1985 | Barlian et al. ................. 73/336 |
| 4,942,364 A | * 7/1990 | Nishijima et al. ........... 324/696 |
| 5,247,827 A | * 9/1993 | Shah .......................... 73/28.01 |
| 5,334,973 A | 8/1994 | Furr ............................ 340/604 |
| 5,369,995 A | 12/1994 | Scheinbeim et al. ...... 73/335.02 |
| 5,384,562 A | 1/1995 | Greenfield ................... 340/584 |
| 5,796,345 A | 8/1998 | Leventis et al. ............. 340/604 |
| 5,903,222 A | 5/1999 | Kawarizadeh et al. ...... 340/604 |
| 6,175,310 B1 | 1/2001 | Gott ............................ 340/605 |
| 6,526,807 B1 | * 3/2003 | Doumit et al. ........... 73/40.5 R |

* cited by examiner

Primary Examiner—Daniel Wu
Assistant Examiner—Samue J. Walk
(74) Attorney, Agent, or Firm—Antonio R. Durando; Quarles & Brady Streich Lang LLP

(57) ABSTRACT

A tape-drive condensation sensor includes a probe with first and second spaced-apart electrodes that define a passage for air flow within a pneumatic conduit. A voltage source is coupled between the electrodes and the voltage of the source and the spacing between the electrodes are adapted to pass a current when a drop of condensation forms between the electrodes. An alarm circuit is activated by the flow of current, the alarm being adapted to signal an event of discernible condensation.

17 Claims, 3 Drawing Sheets

AIR-CONDUIT CONDENSATION SENSOR

BACKGROUND OF THE INVENTION

1. Field of the Invention

The invention relates to condensation sensors and, in particular, to a sensor for a tape-drive device in a computer library system.

2. Description of the Related Art

It is often a problem that atmospheric water vapor condenses on mechanical or electrical equipment causing corrosion of metal parts. This can occur when air that contains water vapor comes into contact with metal structures that are at a relatively low temperature. Accordingly, equipment exposed to changes in temperature, as well as changes in air pressure, can degrade and ultimately fail as a result of unwanted condensation.

In large computer systems, data storage is often provided by means of cartridges and tape drives. These devices are used within an environment of controlled temperature and humidity to decrease the potential for performance degradation and failure due to corrosion. However, the systems that control temperature and humidity are themselves subject to failure; therefore, it is desirable in critical computer systems to provide some form of backup humidity-sensing capability.

Devices capable of sensing the presence of condensation are known in the art. A typical prior-art sensor, including an alarm, is illustrated in FIG. 1. Such a device 20 consists of a condensation sensor 22 and an alarm circuit 24. The sensor 22 typically comprises thin conductive strips 26A, 26B attached to an insulator surface 28 and positioned so as to define a gap 30 therebetween. The thickness of the conductive strips 26A, 26B is shown greatly exaggerated in FIG. 1 for the purpose of illustrating the structure of the sensor 22, but in a typical prior-art sensor their thickness is arbitrary and plays no appreciable role in the operation of the sensor, so long as a gap is created between them for receiving condensation formed in the environment around the sensor.

It is ordinarily desirable to construct the sensor 22 as small and as thin as possible, so as to not interfere with other structures in close proximity to the sensor. In operation, a first voltage is applied to the conductive strip 26A and a second voltage to the conductive strip 26B, thereby creating a potential difference between them. As a result, if sufficient moisture condenses to fill the gap 30 between the conductive strips 26A and 26B, a current flow is established between them. The alarm circuit 24 is adapted to respond to the current by setting off an alarm. The sensor 20 may be attached to any surface where moisture is undesirable.

While the prior-art sensor 22 of FIG. 1 is generally satisfactory for its intended purpose, several problems with its performance limit the scope of its usefulness. The first problem is that the alarm is set off only after the onset of condensation on the surface of the sensor. Therefore, when the alarm is triggered, condensation may already have occurred at other sensitive parts of the device being protected. Moisture can condense on a surface of interest in a device, such as the head of a drive, before it condenses on the sensor 22 if that device is colder than the sensor. Similarly, moisture can condense on another surface at the same time as it condenses on the sensor 22 if the two surfaces are at the same temperature. In either case, the condensation sensor 20 of the prior art at best provides a simultaneous indicator of condensation, which may not be sufficient to properly protect the device by avoiding condensation altogether.

This problem is particularly problematic in the context of tape drives and libraries in large computer systems, such as mainframe computers, that are sensitive to all environmental conditions. Accordingly, these systems are normally situated in computer rooms with environmental-control systems whereby temperature and humidity can be set and maintained precisely. However, as a result of human error or of malfunction of the control systems, environmental conditions that produce condensation on tape drives and other sensitive components can and often do still occur.

In theory, once a condensation sensor of the type shown in FIG. 1 detects moisture and the alarm is set off, the environmental system can be adjusted to prevent condensation. However, by the time the alarm is set off, condensation is likely to have already occurred on surfaces that are at the same temperature of or colder than the sensor, as mentioned above. In addition, further condensation continues to form until the environmental conditions have actually changed to safe levels. This lag time can be significant, especially if the adjustment of environmental parameters is performed manually by an operator who may be slow to respond to a warning because of inadvertence or error.

Moreover, even after the environmental conditions have changed, it may take considerable additional time before the moisture that has already condensed actually evaporates. When the air temperature is only a few degrees above the dew point (that is, when the air is only slightly less humid than at saturation), the rate of evaporation is very slow. Thus, another limitation of prior-art sensors is that condensation can remain on sensitive surfaces for significant periods of time after detection within a protected environment. Since the presence of even small amounts of moisture for limited time periods can be undesirable, this is a significant disadvantage.

A second problem with prior-art sensors of the type illustrated in FIG. 1 in the context of tape-drive protection is that for best results the sensor needs to be mounted on or near the head of the tape drive. This may not always be possible because tape drives are complex mechanisms with many components and, at the very least, the process of adding a sensor complicates the design of the drive. Therefore, condensation sensors are typically installed on stationary structures in the vicinity of the protected device, often at a sight that may or may not reflect the environmental conditions of the device of interest.

Accordingly, there is still a need for a condensation sensor that is capable of detecting when the environment of a protected device approaches the conditions required for condensation of air moisture, so that a warning in advance of the actual onset of condensation can be provided. In addition, there is a need for a condensation sensor that can detect the potential for condensation at the sight of a device of interest without having to be mounted on the device itself.

BRIEF SUMMARY OF THE INVENTION

An objective of the invention is a sensor that detects the potential for condensation on a device at the onset of the conditions leading to condensation, preferably prior to the actual formation of water droplets on the device.

Another objective is a sensor that is particularly suitable for anticipating and preventing condensation on devices that utilize pneumatic control systems, such as tape drives.

A final objective is a condensation sensor that can be adapted for use on a variety of devices without requiring any change to the design of the device of interest.

According to these and other objectives, the present invention consists of a probe that includes first and second spaced-apart electrodes that define a passage for air flow. A voltage source is coupled between the electrodes, and the voltage and the spacing between the electrodes are adapted to pass a current from one of the electrodes to the other through a drop of condensation formed in a gap therebetween. An alarm circuit is activated by the flow of current and is adapted to signal such an event of discernible condensation to an operator or an automated environmental-control system.

The foregoing and other objectives, features, and advantages of the invention will be more readily understood upon consideration of the following detailed description of the invention, taken in conjunction with the accompanying drawings and claims. However, such drawings, description and claims disclose only some of the various ways in which the invention may be practiced.

DESCRIPTION OF THE PREFERRED EMBODIMENT OF THE INVENTION

This invention is based on the realization that several advantages can be obtained by placing a condensation sensor within an airflow stream in the vicinity of a protected device. As a result, the onset of condensation is more likely to be detected prior to actual formation of water droplets on the device.

Figure 1:
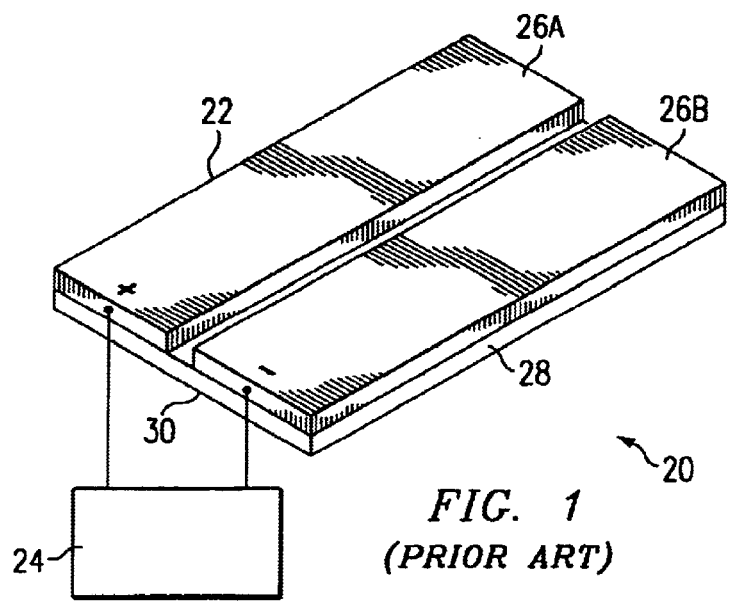
FIG. 1 illustrates a typical prior-art condensation sensor.
Figure 2:
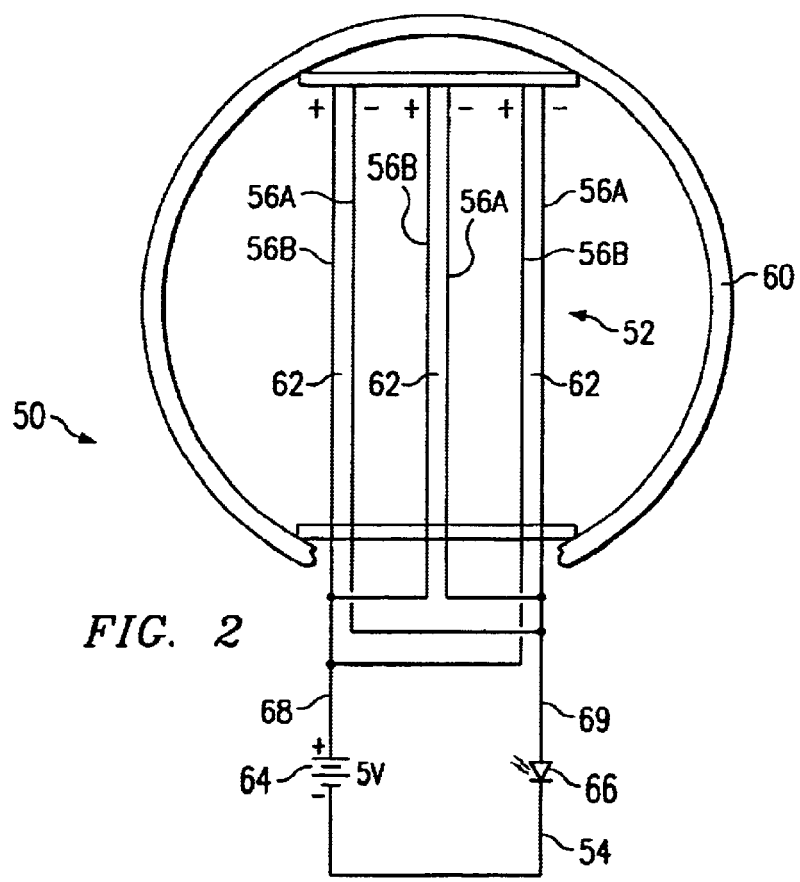
FIG. 2 illustrates a front-side view of one embodiment of a condensation sensor in accordance with the present invention shown mounted in an air conduit.
Figure 3:
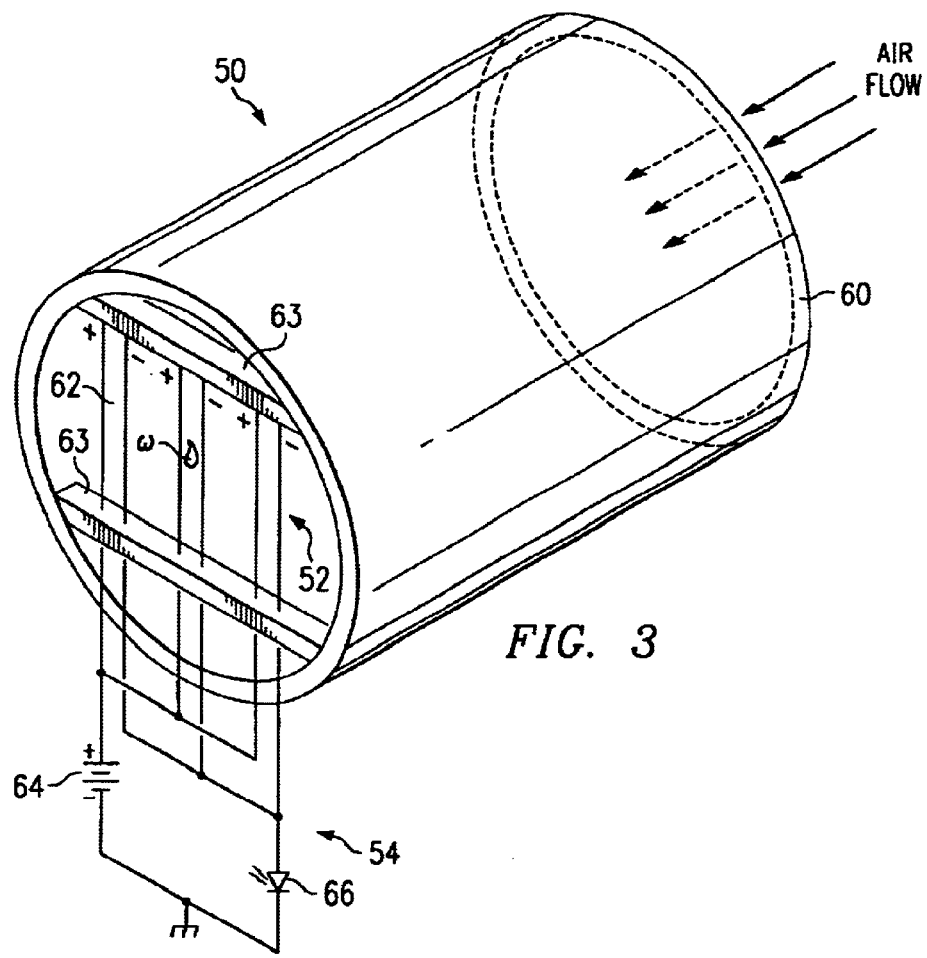
FIG. 3 illustrates a perspective view of the condensation sensor and alarm of FIG. 2.

Referring to the drawings, wherein like parts are designated throughout with like numerals and symbols, FIGS. 2 and 3 illustrate a condensation sensor in accordance with the present invention and generally designated by reference numeral 50. The condensation sensor 50 includes an alarm circuit 54 and a probe 52 mounted within an air conduit 60. The probe 52 is shown as including three pairs of electrodes 56A, 56B, but it could equivalently include more or fewer pairs. The electrodes may have rounded or flat sides and are positioned in spaced-apart configuration, so that each pair defines a passage 62 for airflow in either direction within the conduit 60. Preferably, each electrode consists of a segment of conventional wire mounted between opposing non-conductive support plates 63. Each pair of electrodes is preferably spaced apart no more than 1 mm, optimally about 0.1–0.3 mm.

As shown in FIG. 2, the alarm circuit 54 includes a voltage source 64 and an alarm indicator, such as an LED 66. A first terminal 68 of the alarm circuit 54 is coupled to each of the electrodes 56A and a second terminal 69 is coupled to each of the opposite electrodes 56B.

In operation, the voltage source 64 establishes a voltage potential difference between each pair of electrodes 56A, 56B. Accordingly, if a drop of water W condenses between any of the electrode pairs, as illustrated in FIG. 3, a current is passed from one electrode to the other and causes the LED 66 to light. Thus, the LED serves as an alarm signal. As one skilled in the art would readily recognize, alarm circuits providing different forms of signaling may be equivalently employed as desired. For example, the alarm circuit may be adapted to provide an audible signal or an iconic symbol on a computer monitor, or may provide an input to a computer program or to an automatic control device.

The electrodes 56A and B are preferably positioned vertically and in parallel, so as to increase the chance of accumulation of condensation at the bottom of each pair of wires. That notwithstanding, because of the screen effect provided by the plurality of wires positioned across the section of the conduit 60, droplets of water may form anywhere between two electrodes and immediately trigger the alarm. Therefore, this embodiment of the invention is preferred.

Figure 4:
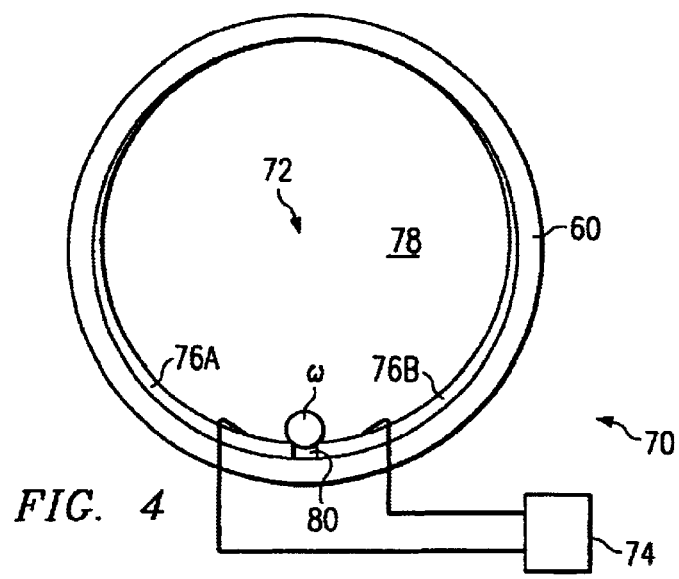
FIG. 4 illustrates a front-side view of a second embodiment of a condensation sensor according to the invention mounted in an air conduit.
Figure 5:
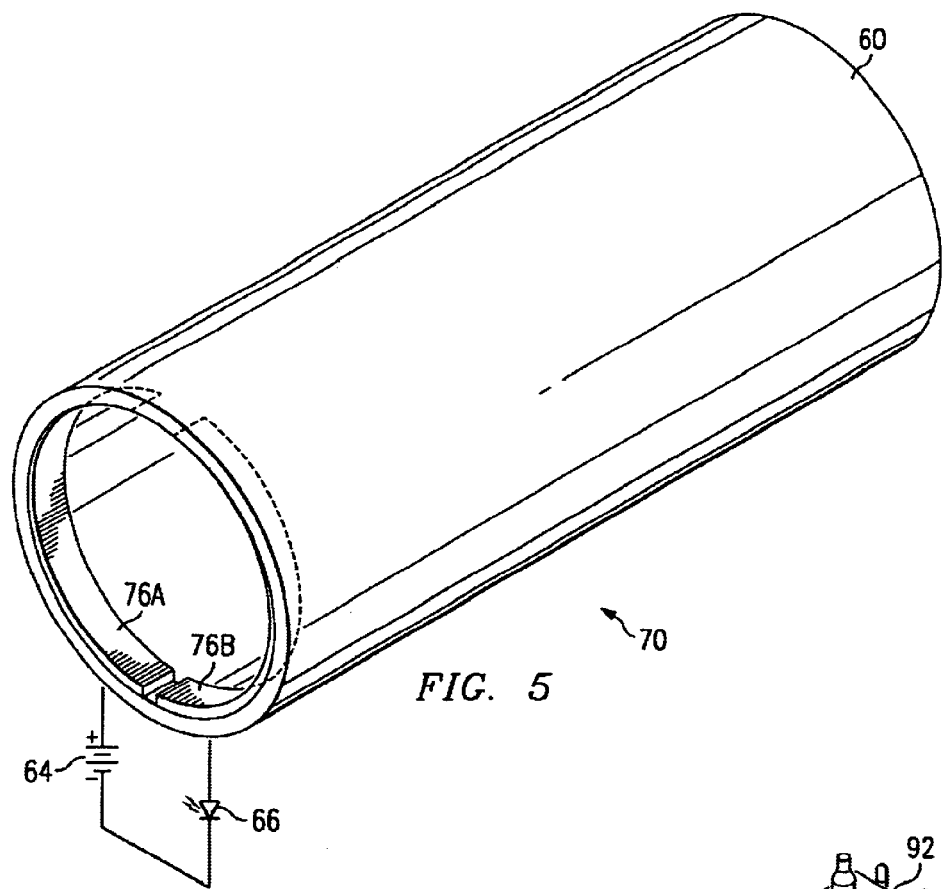
FIG. 5 illustrates a perspective view of the condensation sensor of FIG. 5 mounted in an air conduit.

Turning now to FIGS. 4 and 5, an alternative embodiment of a condensation sensor and alarm unit in accordance with the invention is illustrated, and generally designated by reference numeral 70. The unit 70 includes a probe 72 and a alarm circuit 74. The probe 72 is mounted within an air conduit 60 and includes a pair of electrodes 76A, 76B formed in arc shape to conform to the interior of the air conduit. The electrodes 76A, 76B define a passage 78 for airflow and are spaced apart to form a gap 80 for collection of water condensation. If water drops form as the result of condensation anywhere along the span of the electrodes 76A, 76B, gravity causes them to flow toward the gap 80. If sufficient condensation forms to fill the gap, the probe 72 becomes electrically coupled to the alarm circuit 74 to activate an alarm, which operates in the same manner as described above with reference to the previous embodiment of the invention. The gap 80 is preferably no more than 1 mm wide.

Figure 6:
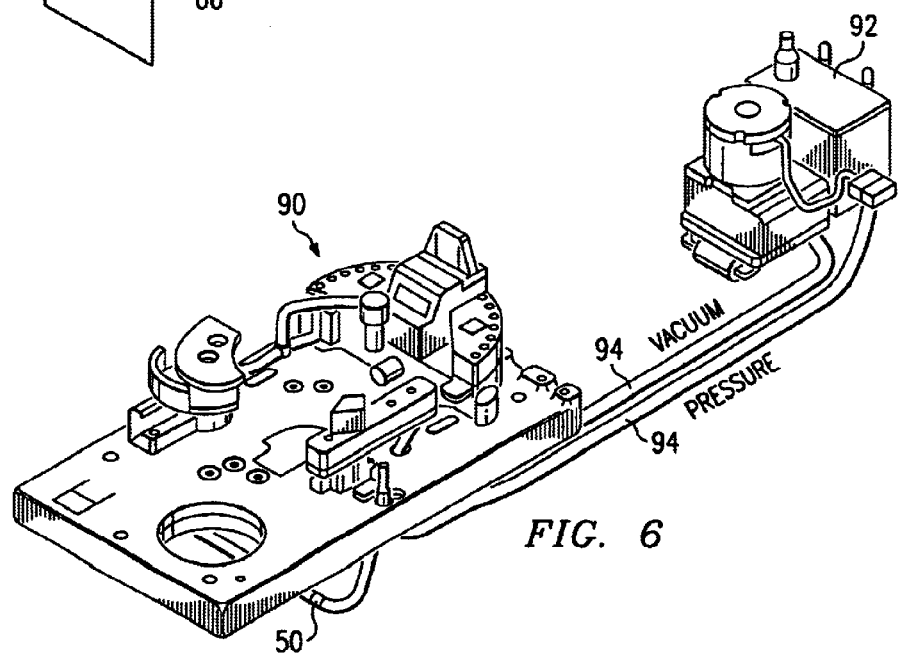
FIG. 6 illustrates a perspective view of a tape drive and a corresponding pneumatic system showing the location where a condensation sensor according to the invention may be mounted.

Referring to FIG. 6, a partial view of an IBM 3590 tape drive 90 is illustrated, including a pneumatic pump 92 that provides vacuum and pressure to the drive through air conduits 94. As shown in the portion of the figure referenced as detail A, a condensation sensor 50 according to the invention may be advantageously mounted in one of the conduits 94, preferably on the pressure side of the system. In the typical operation of a tape drive, a cartridge enclosing a reel of magnetic tape is inserted into the drive and an arm engages the end of the magnetic tape. The magnetic tape is pulled from the tape cartridge, threaded around various rollers, and spooled onto a take-up reel. The path that the magnetic tape takes brings it adjacent to, or in contact with, a head used to read the magnetic tape. The tape drive causes the magnetic tape to travel back and forth across the head to desired read points. Thus, the tape is placed under high tension variations by the tape drive to accommodate high speed tape movement and abrupt stops.

In order to minimize friction along the tape path which produces wear and, ultimately, could cause the failure of the magnetic tape, pressurized air is directed through the air conduit 94 toward the magnetic tape at points where tape contact with the surface is not desired. For example, pressurized air is typically used to provide an air bearing between the magnetic tape and the magnetic tape head. Typically, the air provided in the conduit is also of a controlled humidity and temperature in order to reduce or eliminate the formation of condensation on tape-drive surfaces over which the air passes.

While the condensation sensor and alarm of the invention may be attached to any surface, it is advantageous to install the probe within the interior of the air conduit 94. The invention is in part based on the recognition that a condensation sensor is more effective within an air conduit because flowing air is necessarily at a higher pressure than outside the conduit. Since the dew point of air increases with pressure (all else being equal), condensation will occur at a slightly higher temperature in air flowing in the conduit. Therefore, the probe 52 (FIG. 2) is likely to detect the onset of condensation prior to actual formation of water droplets downstream of the conduit, where the air is prevalently stationary and at a lower pressure.

Moreover, the configuration of the probe 52 (FIG. 2), which allows air to flow between pairs of electrodes, is particularly advantageous in this environment because its thin-wire structure presents a minimal surface to obstruct air flow. Therefore, the probe produces negligible back pressure or other interference in the operation of the pneumatic system of the tape drive. The probe 72 of the second embodiment of the invention (FIG. 4) is similarly suitable for installation in a cylindrical conduit because it does not materially affect the overall geometry or functioning of the system. Because of the relatively large area and the sloped configuration of the electrodes 76A and B, the accumulation of condensation at the bottom of the conduit is favored.

The terms and expressions that have been employed in the foregoing specification are used as terms of description and not of limitation, and are not intended to exclude equivalents of the features shown and described, or of portions thereof. Accordingly, the scope of the invention is intended to be defined and limited only by the claims that follow.

What is claimed is:

1. A vapor-condensation sensor unit, comprising:
   an air conduit for receiving a flow of air and directing the air to a predetermined location;
   a probe including first and second spaced-apart electrodes defining a passage for airflow therebetween in said air conduit, wherein said electrodes include substantially parallel, vertical wires having elongated axes;
   a voltage source, coupled between said electrodes, wherein a voltage of said voltage source and a spacing between said electrodes are adapted to pass a current between the electrodes when vapor condensation forms in said spacing; and
   an alarm circuit adapted to be activated by said current for signaling the presence of said vapor condensation.

2. The sensor unit of claim 1, wherein said spacing between the first and second electrodes does not exceed one millimeter.

3. A vapor-condensation sensor unit, comprising:
   an air conduit for receiving a flow of air and directing the air to a predetermined location;
   a probe including first and second spaced-apart electrodes defining a passage for airflow therebetween in said air conduit, wherein at least one of said electrodes includes an arc-shaped member conforming substantially to an interior surface of said conduit;
   a voltage source, coupled between said electrodes, wherein a voltage of said voltage source and a spacing between said electrodes are adapted to pass a current between the electrodes when vapor condensation forms in said spacing; and
   an alarm circuit adapted to be activated by said current for signaling the presence of said vapor condensation.

4. The sensor unit of claim 3, wherein each of said electrodes includes a member with a curved surface substantially conforming to an interior surface of said conduit.

5. The sensor unit of claim 3, wherein said spacing between the first and second electrodes does not exceed one millimeter.

6. The sensor unit of claim 4, wherein said spacing between the first and second electrodes does not exceed one millimeter.

7. A tape drive for a computer system, comprising:
   a tape drive;
   an air conduit for receiving a flow of air and directing the air to a predetermined location within the tape drive;
   a probe including first and second spaced-apart electrodes defining a passage for airflow therebetween in said air conduit;
   a voltage source, coupled between said electrodes, wherein a voltage of said voltage source and a spacing between said electrodes are adapted to pass a current between the electrodes when vapor condensation forms in said spacing; and
   an alarm circuit adapted to be activated by said current for signaling the presence of said vapor condensation.

8. The tape drive of claim 7, wherein said first and second electrodes are wires having elongated axes.

9. The tape drive of claim 8, wherein the elongated axes of said first and second electrodes are parallel to one another.

10. The tape drive of claim 9, wherein said elongated axes of said first and second electrodes are substantially vertical.

11. The tape drive of claim 7, wherein said first and second electrodes are curved members shaped to follow a contour of said air conduit.

12. A method for sensing condensation in a computer system, comprising the steps of:
    providing a conduit for delivering air to a predetermined location in a device of the computer system;
    providing first and second spaced-apart electrodes defining a gap in said conduit;
    energizing said electrodes; and
    sensing a current passing through said electrodes to indicate a presence of condensation in said gap that establishes electrical contact between the electrodes.

13. The method of claim 12, wherein said first and second electrodes are wires having elongated axes.

14. The method of claim 13, wherein the elongated axes of said first and second electrodes are parallel to one another.

15. The method of claim 14, wherein said elongated axes of said first and second electrodes are substantially vertical.

16. The method of claim 10, wherein said first and second electrodes are curved members shaped to follow a contour of said air conduit.

17. The method of claim 14, wherein said device is a tape drive.

* * * * *